US006489463B1

(12) United States Patent
Zetter et al.

(10) Patent No.: US 6,489,463 B1
(45) Date of Patent: *Dec. 3, 2002

(54) THYMOSIN β-15 PROMOTER AND USES THEREOF

(75) Inventors: Bruce R. Zetter, Wayland, MA (US); Lere Bao, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,052

(22) Filed: Apr. 13, 2000

Related U.S. Application Data

(63) Continuation of application No. PCT/US98/21671, filed on Oct. 14, 1998.
(60) Provisional application No. 60/062,969, filed on Oct. 16, 1997, now abandoned.

(51) Int. Cl.$^7$ .............................................. C07H 21/04
(52) U.S. Cl. ..................... 536/24.1; 435/320.1; 514/44
(58) Field of Search ............................... 536/23.1, 24.1; 435/320.1; 514/44

(56) References Cited

U.S. PATENT DOCUMENTS

| 5,663,071 A | * | 9/1997 | Zetter et al. | 435/325 |
| 5,721,337 A | * | 2/1998 | Zetter et al. | 530/300 |
| 5,831,033 A | * | 11/1998 | Zetter et al. | 530/387.9 |
| 6,017,717 A | * | 1/2000 | Zetter et al. | 435/7.1 |

FOREIGN PATENT DOCUMENTS

| WO | WO 95 05835 A | 3/1995 |
| WO | WO 97 04805 A | 2/1997 |

OTHER PUBLICATIONS

Bao, L, et al, 2000, Molecular cloning and structural characterization of the rat thymosin beta15 gene, Gene, vol. 260, No. 1–2, pp. 37–44*

Bao, L, et al, 1998, Thymosin beta15 expression in tumor cell lines with varying metastatic potential, Clinical and Experimental Metastasis, vol. 16, No. 3, pp. 227–233.*

Gold, JS, et al., 1997, Localization and quantitation of expression of the cell motility–related protein thymosin beta15 in human breast tissue, Modern Pathology, vol. 10, No. 11, pp. 1106–1112.*

Mol et al., 1995 "Do Products of the Myc Proto–Oncogene Play a Role in Transcriptional Regulation of the Prothymosin Alpha Gene," *Mol. Cel. Biol.* 15:6999–7009.

S. Varghese et al., 1991, "Rat Thymosin Beta 4 Gene," 266(22):14256–14261.

S–Y Chen et al., 1995, "Design of a Genetic Immunotoxin to Eliminate Toxin Immunogenicity," *Gene Therapy*, 2(2):116–123.

Maxwell et al., 1986, "Regulated Expression of a Diphtheria Toxin A–Chain Gene Transfected into Human Cells: Possible Strategy for Inducing Cancer Cell Suicide," *Cancer Research*, 46:4660–4664.

Vile et al., 1993, "In vitro and in vivo Targeting of Gene expression to Melanoma Cells," *Cancer Research*, 53:962–967.

* cited by examiner

*Primary Examiner*—Anthony C. Caputa
*Assistant Examiner*—Stephen L. Rawlings
(74) *Attorney, Agent, or Firm*—Nixon Peabody LLP

(57) ABSTRACT

The present invention provides a thymosin β15 promoter. The promoter comprises the nucleotide sequence of SEQ ID NO:1 or a fragment thereof capable of expressing an operably linked DNA. A DNA sequence having nucleotides −400 to +1 of FIG. 1 is a preferred fragment. The invention also provides novel assays for identifying compounds useful in the treatment of malignancies involving modulation of thymosin β15 expression, e.g., breast, pancreas and prostate cancer. The invention further provides a method of human gene therapy for treating malignancies involving up-regulation of thymosin β15 expression.

7 Claims, 1 Drawing Sheet

```
                                                       gtgtcccgtatg
-559   tagaaatgttcaggagtcaggagtggatggccctgaaccactggcttcac -501   atctgtactatgaactggccagagttagaacacaggctactgagcatagg -459   ttcaaaaccactggtcattatagtatggtcctttcccaaggctgcattta -409   aaagcaaaaacaaaaccaaaaatgcaggatacaactaattcagtttggcc -359   cttgaagcacaaatattaaaatctaactggtaagatgtagctgtttaatg -309   tgaggctcctaagttggcagaggaatgaatgtatttgcaaagaaggaatt -259   gtggtcctcaggtctaaagctgtggaagagaaggggaacctaatcttgc c CAAT Box
-209   aataattcgtcccttagccatcagcttataccatgacatcatcaagttct -159   actatgggtgggctgcaggcaactgaacagagactgccttccagaaaact Sp1                CAAT Box
-109   agacggggagggggcgggcaagccagacttgtccaatcagagaggcctgc CRES
-59    gtaggactacgtcaggccgtttgttcaattgtgaagggtgggcagagagt +1
-9     aggggcagaccagttgaagagtTATCAGCTAGTGGCTGCACCCGCGAACA

42     CCACCCTGGTCCGGAGTAGCTGCGGACAGAATTGCTGGCCTAGTAGAAGC

92     TTTGGAACGAGCAG (SEQ ID NO:1)
```

FIG. 1

SEQUENCE LISTING

```
<160> NUMBER OF SEQ ID NOS: 1

<210> SEQ ID NO 1
<211> LENGTH: 676
<212> TYPE: DNA
<213> ORGANISM: Rattus rattus

<400> SEQUENCE: 1
gtgtcccgta tgtagaaatg ttcaggagtc aggagtggat ggccctgaac cactggcttc      60
acatctgtac tatgaactgg ccagagttag aacacaggct actgagcata ggttcaaaac     120
```

-continued

```
cactggtcat tatagtatgg tcctttccca aggctgcatt taaaagcaaa aacaaaacca        180
aaaatgcagg atacaactaa ttcagtttgg cccttgaagc acaaatatta aaatctaact        240
ggtaagatgt agctgtttaa tgtgaggctc ctaagttggc agaggaatga atgtatttgc        300
aaagaaggaa ttgtggtcct caggtctaaa gctgtggaag agaagggaa cctaatcttg         360 ccaataattc gtcccttagc catcagctta taccatgaca tcatcaagtt ctactatggg        420
tgggctgcag gcaactgaac agagactgcc ttccagaaaa ctagacgggg aggggcggg         480 caagccagac ttgtccaatc agagaggcct gcgtaggact acgtcaggcc gtttgttcaa        540
ttgtgaaggg tgggcagaga gtaggggcag accagttgaa gagttatcag ctagtggctg        600
cacccgcgaa caccaccctg gtccggagta gctgcggaca gaattgctgg cctagtagaa        660
gctttggaac gagcag                                                       676
```

THYMOSIN β-15 PROMOTER AND USES THEREOF

This application is a continuation of International Application PCT/US98/21671 filed on Oct. 18, 1998 and which designated the United States, which claims the benefit of U.S. Provisional Application No. 60/062,969 filed Oct. 16, 1997 now abandoned.

GOVERNMENT SUPPORT

This invention was made with government support under Grant No. CA 37393 by the National Institutes of Health (NIH). The government has certain rights in this invention.

BACKGROUND OF THE INVENTION

1. Field of the Invention

The present invention relates to generally to gene promoters. More specifically, the present invention relates to the thymosin β15 promoter and use of this promoter in diagnostic and therapeutic applications as well as in assays for compounds that modulate thymosin β15 expression.

2. Background

Beta thymosins are a family of closely related, highly polar 5 kDa polypeptides. All vertebrates studied and some invertebrates are known to contain one or often two beta thymosins (Nachmias VT, *Curr. Opin. Cell Biol.*, 1993;56–62). Thymosin β15 was recently uncovered in a search for genes with increased expression in motile as compared to poorly motile Dunning rat prostatic carcinoma cell lines (Bao, et al., *Nature Medicine*, 1996; 1322–1328). The protein, which is 5300 Da, was designated thymosin β15 because of its approximately 60% homology with other members of the beta thymosin family.

Thymosin β4 is the most abundant beta thymosin in most mammalian tissue and is the best-studied member of this family. Current understanding is that thymosin β4 sequesters a large pool of monomeric actin that is accessible to be released as needed for polymerization of actin filaments (Cassimeris, et al., *J. Cell Biol.*, 1992;119:1261–70, Weber, et al., *Biochemistry*, 1992;31:6179–85, Nachmias, et al., *Eur. J. Cell Biol.* 1993;61:314–20). Microinjection or overexpression of thymosin β4 has been shown to cause disassembly of actin stress fibers (Sanders, et al., *Proc. Natl. Acad. Sci. USA*, 1992;89:4678–82; Sanger, et al., *Cell Motil. Cytoskeleton*, 1995;31:307–22; Yu, et al., *Cell Motil Cytoskeleton*, 1994;27: 13–25). Like thymosin β4, thymosin β15 binds monomeric actin and inhibits actin polymerization confirming its place in the beta thymosin family. Thymosin β15 also appears to positively regulate cell motility as transfection of antisense thymosin β15 into motile rat prostatic carcinoma lines impairs cell motility in a Boyden chamber apparatus (Bao, et al.).

The putative role of beta thymosin in modulation of the actin cytoskeleton through monomer sequestration suggests that they may be involved in cell differentiation, carcinogenesis and metastasis. In some cell lines, increased thymosin β4 protein or mRNA has been shown to correlate with differentiation, while in most others it has not (Safer, et al., *Bioessays*, 1994; 16:473–9). In human tumors, thymosin β4 mRNA has been shown to be increased in hairy cell leukemia and reduced in some lymphomas (Otero, et al., *Biochem Biophys. Acta.*, 1993; 1176:59–63). Two out of three metastatic colorectal carcinomas showed decreased thymosin β4 mRNA compared to non-metastatic tumors with the third metastatic tumor showing little change (Yamamoto, et al., Biochem *Biophys. Res. Commun*, 1993; 193:706–10). Thymosin β10 mRNA levels are increased in renal cell carcinomas (Hall, AK, *Ren. Fail*, 1994; 16:243–54, Hall, AK, *Cell Mo. Biol. Res. Commun*, 1995;41:167–80), and thymosin β10 up-regulation was shown to correlate with the metastatic potential of melanomas (Weterman, et al., Int. J Cancer, 1993; 53:278–84). The expression of each thymosin beta family member is independently regulated. Consequently different family members may be independently elevated or decreased in particular tumor types. As thymosin β15 has only recently been described, it is less well characterized. It is present in very few normal adult tissues but was shown to be up-regulated in metastatic human prostate cancers at both the mRNA and protein level as compared to less metastatic prostate cancers (Bao, et al.). Immunostaining of human prostate cancer cases revealed a general correlation between Gleason grade and thymosin β15 expression, with high grade tumors (Gleason grade 8–10) showing increased staining compared to low grade tumors (Gleason grade 2–5).

Thymosin β15 was also up-regulated in 15/20 human pancreatic tumors. Additionally, thymosin β15 has been shown to be up-regulated in malignant as compared with benign breast tissue and may represent an early marker for breast malignancy (Gold, et al., *Modem Pathology* 1997, In press). The restricted distribution of thymosin β15 may allow targeted destruction of malignant tumors expressing the protein e.g., prostate, breast and pancreatic tumors.

SUMMARY OF THE INVENTION

The present invention provides a thymosin β15 promoter. The promoter comprises the nucleotide sequence of SEQ ID NO: 1 or a fragment thereof capable of expressing an operably linked DNA. A DNA sequence having nucleotides −400 to +1 of FIG. 1 (nucleotide 153–572 of SEQ ID NO: 1) is a preferred fragment.

The invention further provides a vector having the promoter of the present invention operably linked to a DNA encoding a gene product and host cell containing such vectors. These gene products can be marker genes, toxins, suicide genes, viral genes, ribozymes, intrabodies, antisense, or another heterologous gene product.

The invention also provides novel assays for identifying compounds useful in the treatment of malignancies involving modulation of thymosin β15 expression, e.g., breast, pancreas and prostate cancer. Preferred compounds identified through assays of the invention can modulate, particularly inhibit, thymosin β15. A preferred assay comprises transfecting a host cell with a vector containing the thymosin β15 promoter operably linked to a gene encoding a reporter or marker protein; contacting the cell with a test compound and measuring reporter protein expression.

The invention also provides a method of human gene therapy for treating malignancies involving up-regulation of thymosin β15 expression, e.g., breast, pancreas and prostate cancer. The method comprises administering to a human in need thereof an expression vector comprising the thymosin β15 promoter operably linked to a DNA encoding a gene product the expression of which by the cell expressing thymosin β15, i.e., the cancer cells, inhibits the growth of the cell or results in the cells death. Such gene products include, for example, toxins, suicide genes, ribozymes, intrabodies, or antisense DNA or RNA.

Other aspects of the invention are disclosed infra.

BRIEF DESCRIPTION OF THE DRAWINGS

FIG. 1 shows the nucleotide sequence (SEQ ID NO: 1) of β15 genomic DNA containing the thymosin β15 promoter region.

DETAILED DESCRIPTION OF THE INVENTION

We have now isolated the thymosin β15 promoter. The promoter comprises the nucleotide sequence of SEQ ID NO: 1 or a fragment thereof capable of expressing an operably linked DNA, e.g., a DNA encoding of marker protein.

The thymosin β15 promoter of the present invention may be part of an expression vectors and may be incorporated into recombinant cells for expression and screening, transgenic animals for functional studies (e.g. the efficacy of candidate drugs for disease associated with expression of thymosin β15), etc.

Nucleic acids comprising the promoter of the present invention are isolated, meaning the nucleic acids comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The promoter of the present invention find a wide variety of applications including: use as hybridization probes, PCR primers, and use in gene therapy applications.

For example, to reduce thymosin β15 activity, nucleic acids capable of inhibiting thymosin β15 expression may be administered to a patient in need thereof. These nucleic acids may include for example, antisense DNA or RNA or ribozymes.

Additionally, the thymosin β15 promoter may be used in a method of human gene therapy for treating malignancies involving up-regulation of thymosin β15 expression, e.g., breast and prostate cancer. The method comprises administering to a human in need thereof an expression vector comprising the thymosin β15 promoter operably linked to a DNA encoding a negative potentiator, i.e., a gene product the expression of which by the cancer cell inhibits the growth of the cell or results in the death of the cell.

Negative potentiators include toxins, antisense RNA or DNA, a suicide gene such as HSV thymidine kinase (tk), ribozymes, dominant-negative mutants, cytotoxins, an antibody such as an antibody with an intracellular localization signal (intrabody). Toxins and suicide genes are more preferred. For example, when the negative potentiator is a toxin, one preferably takes care to alter the toxin gene to minimize its potential to affect nontargeted cells. This can be done by standard techniques such as deleting those sequences encoding recognition domains. Toxins are well known and include diphtheria toxin and truncated versions thereof, pseudomonas exotoxin, and truncated versions thereof, ricin/abrin, blocked ricin/abrin, ricin toxinA-chain, ribosome inactivating protein, etc. All these proteins have different domains. For example, the gene encoding PEA has several domains: Domain I is responsible for cell recognition, Domain II for translocation of the toxin cross-membrane and Domain III of (Pseudomonas exotoxin A) for adenosine diphosphate (ADP)-ribosylation of elongation factor 2, which is the step actually responsible for cell death. [Gary, G. L., et al., Proc. Natl. Acad. Sci. USA 81:2645–2649 (1984); Allured, V. S., et al., Proc. Natl. Acad. Sci. USA 83:13220–1324 (1986); Siegall, C. B., et al., J. Biol. Chem. 264:14256–142611989)]. Accordingly, by alterations in Domain I or Domain II, that render those domains incapable of expression, for example, by a frameshift mutation, insertion of termination sequences, or deletions one can minimize the ability of the toxin to affect neighboring cells. Thereafter, the skilled artisan can use standard techniques to insure that the other domains, or portions of domains where expression is desired, are used.

For example, as indicated above, with PEA only Domain III is absolutely required. However, partial sequences from other domains makes the toxin more effective. For example, one can prepare PEA mammalian expression vectors in which Domain III (mature PEA amino acid residues 405 to 613) only, is expressed and one which encodes Domain III and partial Domain IB, a sequence of amino acids 385 to 613 is expressed. These sequences should be operably linked to the thymosin β15 promoter, which will permit expression in the target cell. The toxin proteins encoded by these gene fragments lack a recognition domain. They are non-toxic to surrounding cells and are only toxic when expressed inside a cell. These expression vectors can readily be tested to determine how well they express a product intracellularly by a simple in vitro assay. For example, the expression of those DNA sequences encoding PEA toxin fragments can be tested by transforming β15 expressing malignant cells with the vector and observing the cytotoxicity of the cell. Suicide genes such as tk work by sensitizing the cell to a compound which the cell would otherwise not be affected by, e.g. ganciclovir. One preferred type of antibodies works by binding to a target intracellularlly (e.g. an intrabody). For example, by targeting a gene product that is overexpressed in malignant cells such as thymosin β15.

The promoter of the present invention may further be used to activate viruses e.g., adenovirus, that have been modified so that their replication is regulated by a transactivation signal produced by the diseased host cell. For example, the viruses may be designed to selectively replicate in and kill tumor cells expressing thymosin β15, but not normal cells. [PCT/US96/12294, the disclosure of which is incorporated herein by reference.]

The vectors comprising the thymosin β15 promoter are introduced into the target cell, i.e., a cell expressing thymosin β15, by any method which will result in the uptake and expression of the nucleic acid by the target cells. These can include vectors, liposomes, naked DNA, adjuvant-assisted DNA, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpes virus vectors such as a herpes simplex I virus (HSV) vector [A. I. Geller et al., *J. Neurochem,* 64:487 (1995); F. Lim et al., in *DNA Cloning: Mammalian Systems*, D. Glover, Ed. (Oxford Univ. Press, Oxford England) (1995); A. I. Geller et al., *Proc Natl. Acad. Sci.*: U.S.A.:90 7603 (1993); A. I. Geller et al., *Proc Natl. Acad. Sci USA:* 87:1149 (1990)], Adenovirus Vectors [LeGal LaSalle et al., *Science,* 259:988 (1993); Davidson, et al., Nat Genet., 3:219 (1993); Yang et al., *J. Virol.,* 69: 2004 (1995)]

and *Adeno-associated Virus Vectors* [Kaplitt, M. G., et al., Nat. Genet, 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $Ca_3(PO_4)_2$ precipitation, DEAE dextran, electroporation, protoplast fusion, lipofecton, cell microinjection, and viral vectors.

The vector can be employed to target essentially any desired target cell, such as a glioma. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed™ Infusion System. A method based on bulk flow, termed convection, has also proven effective at delivering large molecules to extended areas of the brain and may be useful in delivering the vector to the target cell (Bobo et al., *Proc. Natl. Acad. Sci. USA*, 91:2076–2080 (1994); Morrison et al., *Am. J. Physiol.*, 266: 292–305 (1994)). Other methods that can be used include catheters, intravenous, parenteral, intraperitoneal and subcutaneous injection, and oral or other known routes of administration.

The invention provides efficient screening methods to identify pharmacological agents or lead compounds for agents which modulate, e.g. interfere with or increase thymosin β15 activity. The methods are amenable to automated, cost-effective high throughput drug screening and have immediate application in a broad range of pharmaceutical drug development programs.

A preferred assay mixture of the invention comprises a host cell transfected with a vector containing the thymosin β15 promoter operably linked to a gene encoding a reporter or marker protein. Preferred marker proteins include reporters such as β-galactosidase, chloramphenicol acetyltransferase (CAT) and luciferase. An assay mixture of the invention also comprises a candidate pharmacological agent. Generally a plurality of assay mixtures are run in parallel with different candidate agent concentrations to obtain a differential response to the various concentrations. Typically, one of these assay mixtures serves as a negative control, i.e. at zero concentration or below the limits of assay detection. Candidate agents encompass numerous chemical classes, though typically they are organic compounds and preferably small organic compounds. Small organic compounds suitably may have e.g. a molecular weight of more than about 50 yet less than about 5,000. Candidate agents may comprise functional chemical groups that interact with proteins and/or DNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced.

Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc.

A variety of other reagents may also be included in the mixture. These include reagents such as salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

For example, to screen for thymosin β15 expression inhibitors, the resultant mixture is incubated under conditions whereby, but for the presence of the candidate pharmacological agent, the marker protein is expressed. The mixture components can be added in any order that provides for the requisite interactions. Incubations may be performed at any temperature which facilitates optimal interaction of the components, typically between 4° and 40° C., more commonly between 15° and 40° C. Incubation periods are likewise selected for optimal interaction but also minimized to facilitate rapid, high throughput screening, and are typically between 0.1 and 10 hours, preferably less than 5 hours, more preferably less than 2 hours.

After incubation, the presence or absence of the marker is detected by any convenient way.

The present invention is further illustrated by the following Examples. These Examples are provided to aid in the understanding of the invention and are not construed as a limitation thereof.

EXAMPLE 1

Materials and Methods

Genome Walking of 5'-Region which contains Tβ15 promoter: 5 µg of rat genomic DNA was digested in 100 µl reaction volumes with 80 U of restriction enzymes EcoR I, Sca I, Dra I, and Pvu II overnight at 37° C. separately. The DNA was phenol/chloroform extracted, ethanol precipitated, and dissolved in 20 µl of 10 mM Tris-HCl, pH 7.5, 0.1 mM EDTA. 10 µl of DNA was then ligated to 5 µM adaptor (Clontech) in a volume of 20 µl overnight at 16° C. The ligation reaction was terminated by incubation of the tubes at 70° C. for 5 min, then diluted 10-fold by addition of 180 µl of 10 mM Tris-HCl, pH7.5 1 mM EDTA. Primary PCR amplifications were conducted in 50 µl volumes containing 1 µl of ligated and diluted DNA, 0.4 µM adaptor primer AP1 and gene-specific primer. The cycle parameters were as follows; denaturation at 94° C. for 30 sec and annealing/extension at 68° C. for 35 cycles of PCR were used.

A secondary PCR reaction was conducted with 1 µl of a 50-fold dilution of the primary PCR using adaptor primer AP2 and the nested gene-specific primer. The same reaction composition and cycle parameters were used and 25 thermocycles performed. PCR products were examined on 0.8% agarose/EtBr gels, and subsequently cloned by TA cloning system.

DNA Sequencing- Sequencing was carried out by the dideoxy chain termination method using the Sequenase™ Version 2.0 Sequencing Kit (U.S. Biochemical, Cleveland, Ohio) with $^{35}$S dATP (New England Nuclear Wilmington, Del.) following manufacturer's instructions. The nucleotide sequences were determined for both DNA strands.

Primer Extension Analysis—A synthetic oligonucleotide primer representing the antisense sequence of Tβ15 cDNA from bases 12 to 43 in FIG. 1 was end-labeled with [γ$^{32}$P]ATP (3000 Ci/mmol, New England Nuclear) by T4 DNA kinase (Amersham). 50 μg of total RNA extracted from AT3.1 cells were hybridized with the end-labeled primer (1×10$^5$ cpm) In 250 mM KCl, 10 mM Tris-Cl (pH 8.3), and 1 mM EDTA at 65° C. for 1 h. Primer extension reactions were initiated by addition of 10 units Moloney Murine Leukemia Virus reverse transcriptase (Life Technologies Inc.) in 75 mM KCl, 10 mM MgCl2, 20 mM Tris-Cl (pH 8.3), 0.25 mM EDTA, 0.25 mM dNTPs and incubated at 42° C. for 1 h. The primer extension products were electrophoresed on a 6% denaturing polyacrylamide gel, with a known DNA sequencing sample in the adjacent lanes to allow determination of the precise length of primer-extention fragments.

Construction and Transfection of the Reporter Vector—To measure promoter activity of the 5'-flanking region by luciferase assay, a reporter vector for transfection was constructed. Luciferase constructs were made by subcloning a Xho I DNA fragment (468 bp) containing the 5'-flanking region and a part of the first exon into a pGL2-basic vector (Promega). The orientation was confirmed by sequence analysis. Cells at 90% confluence (1.0×10$^6$ cells/transfection) were harvested by 0.25% trypsin and transfected with luciferase constructs and promoterless pGL2-basic as well by liperfectamine method. PGK-lacZ, a lacZ reporter plasmid, was used to correct for transfection efficiency. Transfected cells were seeded on 9.0 cm dishes in culture medium for 48 h. After washing with calcium- and magnesium-free phosphate buffered saline twice, the cells were incubated in 900 μl of cell lysis buffer (promega) at room temperature for 15 min. The cell lysate was kept at −80° C. for luciferase assay.

Luciferase Assay—20 μl of the cell lysate was mixed with 100 μl of Luciferase Assay Reagent (Promega) at room temperature. Immediately, the light intensity of the samples was counted in a luminometer (BioOrbit 1251, Pharmacia Biotech) for 20 sec at 25° C. Luciferase concentration was estimated by calculating the square root of measured counts/mm minus background counts/min.

Results

To obtain the promoter region of thymosin β15 gene, a PCR-based GenomeWalker method was used. The GenomeWalker genomic libraries constructed from AT3. 1 cells were amplified using an adaptoe-specific sense primer (Olontech) and an antisense primer specific for exon 1 of thymosin β15. Subsequent amplification of the PCR products with nested primers generated single major products, with an about 500-bp product in Dra I library and a 1.8-kb product in EcoRV library. The sequence of the product from Dra I library was identical to the sequence of 3'-region of the 1.8-kb product from EcoRV library, suggesting that they represent the same thymosin β15 genomic DNA rather than distinct genes. The nucleotide sequence of the product from Dra I library is shown in FIG. 1 Examination of this sequence revealed that within the putative promoter region of 300 bp upstream of exon 1, the sequences were GC-rich (60%) and showed the presence of the following motifs: (i) a canonical SP1 binding site, (ii) a potential binding site for the DNA binding factor CREB and (iii) a putative CAAT box. No prototypical TATA box appeared to be present. This suggests that expression of the thymosin β15 gene may be controlled by a typical housekeeping gene promoter.

To localize the transcription start site of thymosin β15 gene, primer extension analysis was performed with an antisense oligonucleotide and the total RNA from AT3. 1 cells as a template. The major extension product was observed as a band about 60 bp in length.

This product corresponded to the 13 bp upstream of the 3' end of exon 1. The transcription start site is presented by base +1 of the reported sequence (FIG. 1).

To verify whether the genomic fragment flanking the 5' end of rat thymosin β15 cDNA has promoter activity, a genomic fragment corresponding to bp −570 to 60 was coupled to a promoterless luciferase transcription reporter gene and examined for the ability to mediate basal transcription. The rat prostatic carcinoma cell line, AT3. 1, was transiently transfected with reporter constructs, and cell extracts were assayed for luciferase activity 48 h post-transfection. Thymosin β15 sequences fused to the reporter in the appropriate transcriptional orientation (pGL2-5') consistently produced an about 100 fold increase in luciferase activity when compared to a promoterless luciferase construct (pGL2-basic). In contrast, thymosin β15 sequences fused in the opposite transcriptional orientation (PGL2–5' reverse) did not induce a significant level of reporter activity. These results indicate that the 5'-flanking region has a promoter activity. In addition, we also examined the effect of TPA and cpt-cAMP on promoter activity of the 5'-flanking region. TPA (10$^{-6}$ M) up-regulated luciferase activity about 2-fold in pGL2–-5', whereas cpt-cAMP (200 mM) had no effect.

The invention has been described in detail with reference to preferred embodiments thereof. However, it will be appreciated that those skilled in the art, upon consideration of this disclosure, may make modifications and improvements within the spirit and scope of the invention.

What is claimed is:

1. An isolated nucleotide sequence, wherein said nucleotide sequence comprises SEQ ID NO: 1 or a fragment thereof that promotes expression of an operably linked DNA.

2. The nucleotide sequence of claim 1, further comprising an operably linked heterologous DNA.

3. The nucleotide sequence of claim 2, wherein the heterologous DNA encodes a negative potentiator.

4. The nucleotide sequence of claim 3, wherein the negative potentiator is a suicide protein or a cytotoxin.

5. The nucleotide sequence of claim 4, wherein the negative potentiator is a suicide protein and the suicide protein is HSV thymidine kinase.

6. The nucleotide sequence of claim 4, wherein the cytotoxin contains at least Domain III of Pseudomonas exotoxin A.

7. A vector containing the nucleotide sequence of claim 1.

* * * * *